United States Patent [19]
Burkholder et al.

[11] Patent Number: 5,717,220
[45] Date of Patent: Feb. 10, 1998

[54] LANE MONITOR FOR MONITORING DRESSING ON THE SURFACE OF BOWLING LANES

[75] Inventors: Roy A. Burkholder, Whitehall; John R. Edwards, Norton Shores; Shawn R. Gibson, Newaygo, all of Mich.

[73] Assignee: Brunswick Bowling & Billiards Corporation, Muskegon, Mich.

[21] Appl. No.: 609,456

[22] Filed: Mar. 1, 1996

Related U.S. Application Data

[62] Division of Ser. No. 266,423, Jun. 27, 1994, Pat. No. 5,521,393.
[51] Int. Cl.$^6$ .............................. G01N 21/86; A63D 1/04
[52] U.S. Cl. .................. 250/559.22; 250/559.27; 250/552; 250/559.4; 356/381; 473/117
[58] Field of Search .......................... 250/559.2, 559.4, 250/552, 559.27, 559.28; 356/375, 376, 381, 382; 473/115, 117; 427/9, 10

[56] References Cited

U.S. PATENT DOCUMENTS 4,437,010  3/1984  Scheie et al. ..................... 250/459.1
4,487,788  12/1984  Scheie et al. ..................... 427/9
4,674,745  6/1987  Speranza ........................ 473/117
5,521,393  5/1996  Burkholder et al. ............. 250/559.22

Primary Examiner—Stephone B. Allen
Attorney, Agent, or Firm—Wood, Phillips, VanSanten, Clark & Mortimer

[57] ABSTRACT

Time consuming analyzing of the dressing levels on bowling lanes is eliminated through the use of an apparatus that includes a path of travel (48) for a sample strip, a light source (50) on one side of the path (48) and a photosensitive sensor (46) on the other side of the path. A feed roller (60) is journaled adjacent the path and is driven by a stepper motor (58) in predetermined increments. An analog to digital converter (40) is connected to the sensor (36) for receiving analog signals therefrom and converting the same to digital signals. A random access memory (38) is connected to the converter (40) for receiving signals therefrom and for storing data represented by the signals. A central processing unit (34) is provided for operating the motor (58), the sensor (46) and the random access memory (38). Also included is a program storage (38) for storing control algorithms for the central processing unit (34) along with a port (66) connected to the central processing unit (34) for receipt of exteriorally generated commands and for outputting stored or otherwise acquired data.

12 Claims, 15 Drawing Sheets

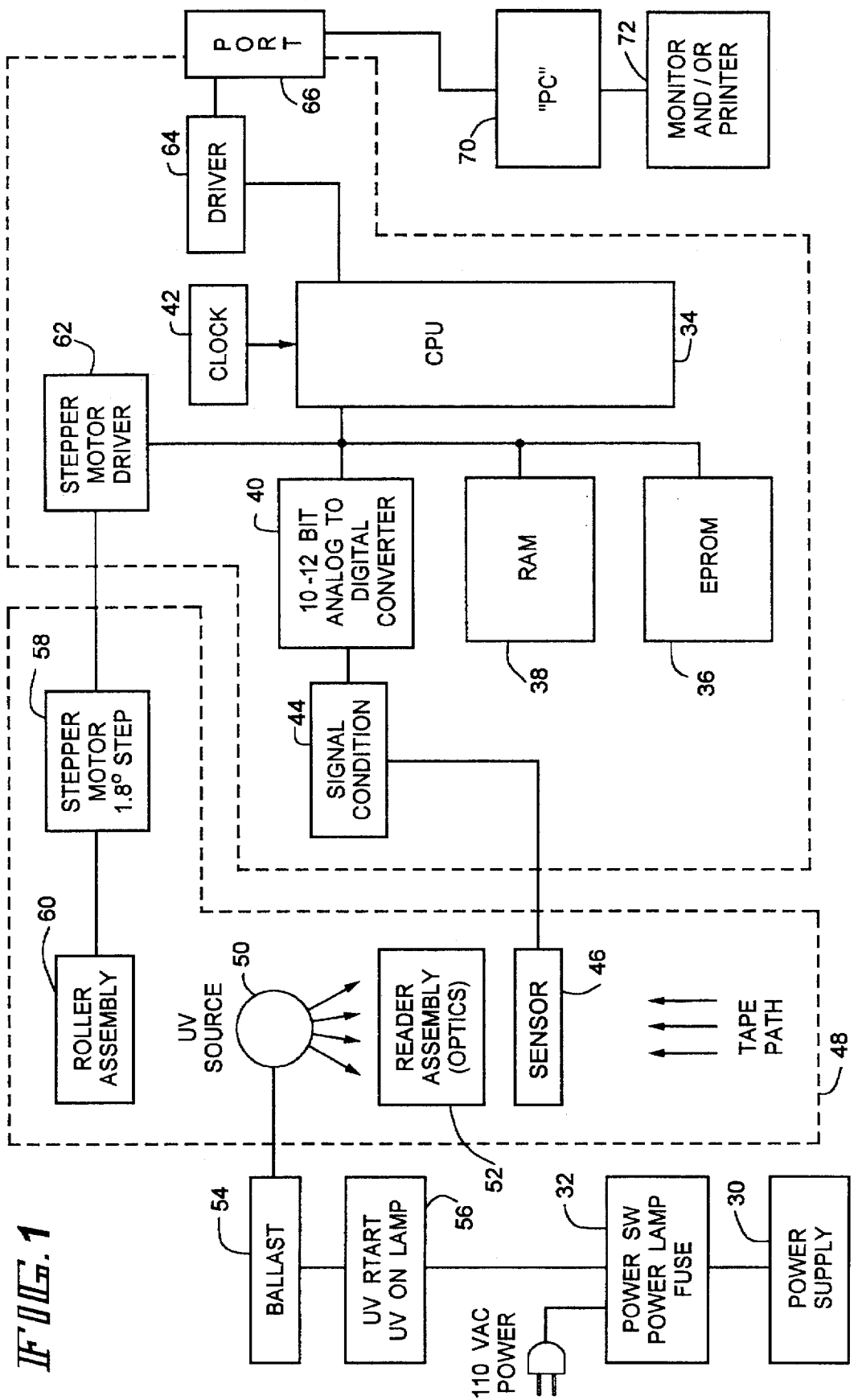

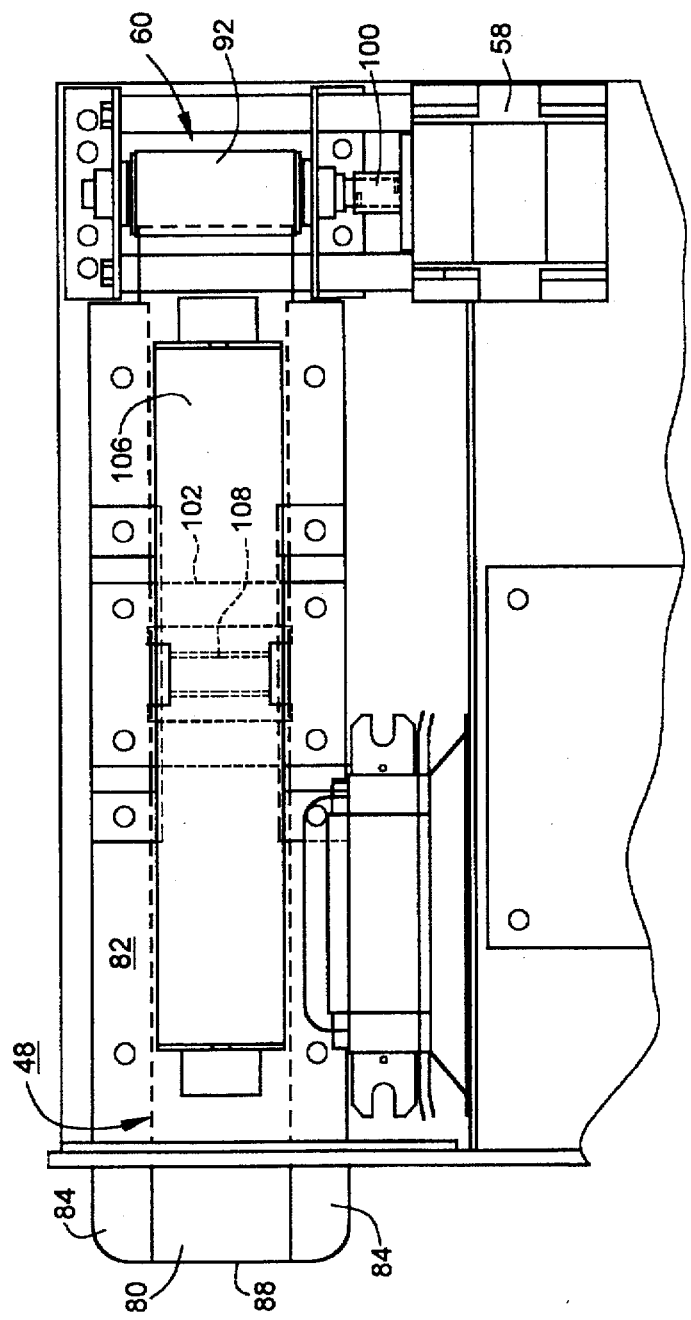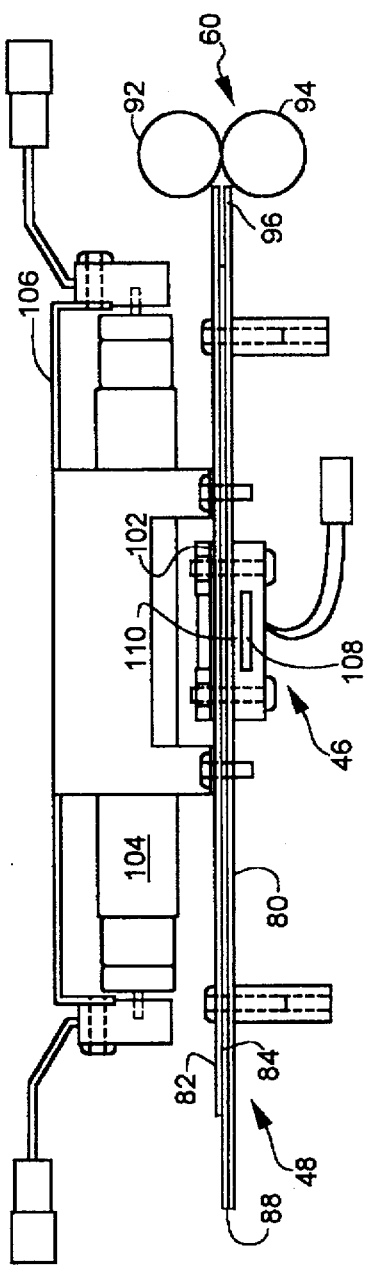

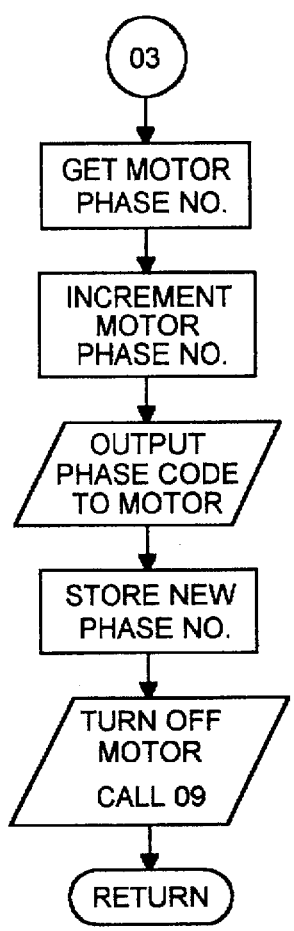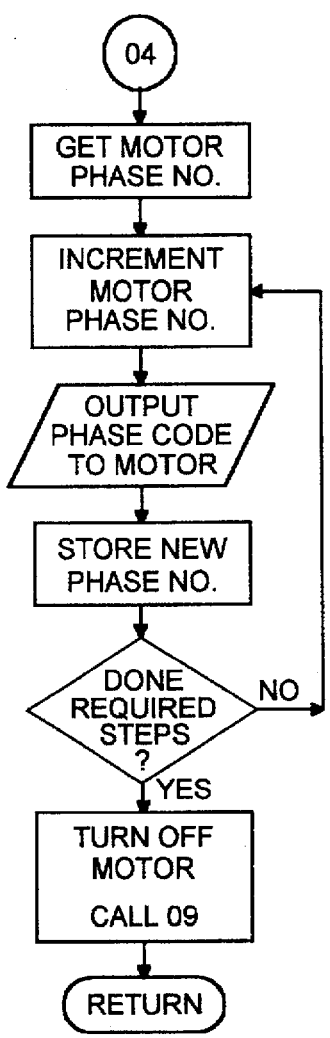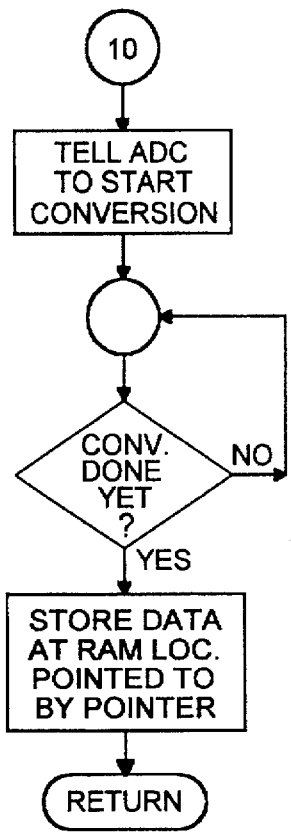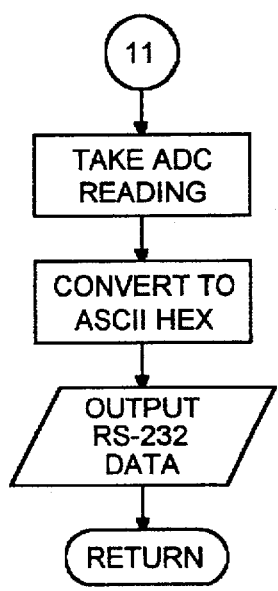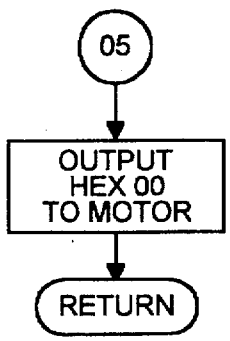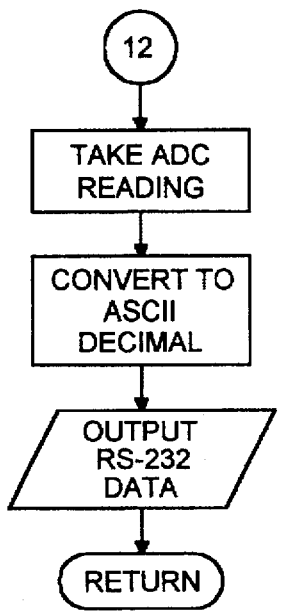

LANE MONITOR FOR MONITORING DRESSING ON THE SURFACE OF BOWLING LANES

This is a division of application Ser. No. 08/266,423 filed Jun. 27, 1994 U.S. Pat. No. 5,521,393.

FIELD OF THE INVENTION

This invention relates to an apparatus that may be employed to monitor the lane dressing on a bowling lane.

BACKGROUND OF THE INVENTION

Commonly assigned U.S. Pat. No. 4,437,010 issued Mar. 13, 1984 to Scheie, et al., the details of which are herein incorporated by reference, discloses a method and apparatus for determining the quantity of conditioner or dressing on the surface of a bowling lane. The apparatus therein disclosed utilizes a double thickness strip of transparent tape as a sample strip. A sample strip is obtained through the use of the apparatus disclosed in commonly assigned U.S. Pat. No. 4,487,788 issued Dec. 11, 1984, also to Scheie, et al., the details of which are herein incorporated by reference. The subject matter of both patents has been commercialized by the assignee of the present application and has met with considerable success in allowing bowling center proprietors to keep track of dressing conditions on their lanes to assure that the lanes meet specifications of the appropriate bowling regulatory group, in the United States, the American Bowling Congress or ABC.

For example, if a bowling center requests certification, the same will be inspected and, if requirements met, a certificate issued. To retain the certificate, the American Bowling Congress specifically states:

"If dressing is used, it shall meet ABC/WIBC specifications and must comply with the following:

Dressing must be distributed from edgeboard to edgeboard for the entire predetermined distance down the lane (for example, and without limiting the distance, 35–40 feet from the foul line). Following any application of dressing, in the dressed portion of the lane, there shall be a minimum of 3 units of dressing at all points on the lane surface. A unit is defined as a measurement of dressing film thickness equivalent to 0.0167 cubic centimeters of dressing per square foot of lane surface as measured by ABC/WIBC approved lane dressing measuring equipment."

Use of commercial embodiments of the subject matter of the two previously identified patents enables a bowling lane proprietor to assure that his lane meets such a specification so as to allow him to retain his certification.

To enable analysis, the ABC specifies that approved lane dressings contain a precise amount of ultraviolet light sensitive dye that will fluoresce when exposed to ultraviolet light. The more dye present, the greater the fluorescence. Thus, by measuring fluorescence, the quantity of dressing can be determined.

Because the measurement must be made "from edgeboard to edgeboard", and a bowling lane is 42" wide, it is necessary to inspect at a plurality of points across the lane. In use, measurements are made at 1⅛" intervals (the width of a board on a conventional bowling lane) for a total of 39 measurements in all. One layer of tape is applied from the 10 pin side of the lane all the way across the lane to the 7 pin edge. At the end board, a one inch, opaque marker is placed on the tape. the tape is extended a few inches further without contacting the lane and then an encapsulating tape strip is applied to the sticky side of the first layer. As a result, a sample containing tape of about 48 inches in length is formed. The 42 inches applied to the lane contains the sample, and that part on the opposite side of the marker serves as a leader for the sample tape when placed in an analyzer. The sample containing tape is advanced through the machine in 1⅛" inch increments by manually turning a knob for a tape drive system that includes detents to provide a perceptible indication that the tape has advanced 1⅛". With each advance of the tape, a meter is read and the value manually recorded. The same may be plotted on a graph or the like to illustrate the distribution of dressing across the lane at the location the sample tape was taken.

While the system works extremely well for it's intended purpose, its use can be time consuming, taking up to 20 minutes to analyze a single sample tape. Moreover, because the system takes but a single reading every 1⅛", there is some possibility that the reading will not be representative of the condition at that particular point, more so than if several readings were taken each 1⅛".

The present invention is directed to overcoming one or more of the above problems.

SUMMARY OF THE INVENTION

It is the principal object of the invention to provide a new and improved lane monitor for monitoring the dressing on a bowling lane surface. More particularly, it is an object of the invention to provide a new and improved lane monitor that reduces the time required to analyze dressing requirements on a lane, has a high degree of accuracy, and is exceptionally "user friendly".

An exemplary embodiment of the invention achieves the foregoing objects in an apparatus for monitoring the dressing on the surface of a bowling lane which includes a strip feeder for feeding a sample strip in a predetermined path, a sensor adjacent the path for sensing a characteristic of a sample strip in the path and issuing a signal representative thereof, a means for operating the strip feeder and the sensor to sense the strip and to issue the signals at a predetermined rate for a predetermined increment of movement of the strip by the feeder and means for collecting the signals and for storing values representing the same.

In a preferred invention, means are provided for reading the collecting and storing means and for displaying the values contained therein.

A preferred embodiment of the invention is particularly adapted for use with a transparent sample strip and includes means defining a path of travel for the strip, a light source on one side of the path and a photosensitive sensor on the other side of the path. A feed roller is journal adjacent the path and a stepper motor is provided for driving the roller in predetermined increments. An analog to digital converter is connected to the sensor for receiving analog signals therefrom and converting the same to digital signals. A random access memory is connected to the analog to digital converter for receiving signals therefrom and for storing data represented by the signals. A central processing unit is provided for operating the motor, the sensor and the motor and a program storage is utilized for storing control algorithms for the central processing unit. A port is also provided which is connected to the central processing unit for receipt of exteriorally generated commands and for outputting data.

In a highly preferred embodiment of the invention, the apparatus includes means for providing a plurality of the analog signals for a predetermined distance of strip movement in the path.

Preferably, the stepper motor drives the strip through the predetermined distance in a plurality of increments equal to the plurality of analog signals and the sensor samples the strip for each such increment.

Other objects and advantages will become apparent from the following specification taken in connection with the accompanying drawings.

DESCRIPTION OF THE DRAWINGS

FIG. 1 is a block diagram of a lane monitor made according to the invention;

FIG. 2 is a plan view of a sensor and sample drive employed in the invention;

FIG. 3 is a side elevation of the sensor and drive;

FIG. 7 is a flow diagram for two subroutines;

FIG. 8 is a flow diagram for four subroutines;

FIG. 9 is a flow diagram for still another subroutine;

FIG. 10 is a flow diagram for still another subroutine;

FIG. 11 is a flow diagram for still another subroutine;

FIG. 12 is a flow diagram for still another subroutine;

DESCRIPTION OF THE PREFERRED EMBODIMENT

Figure 4:
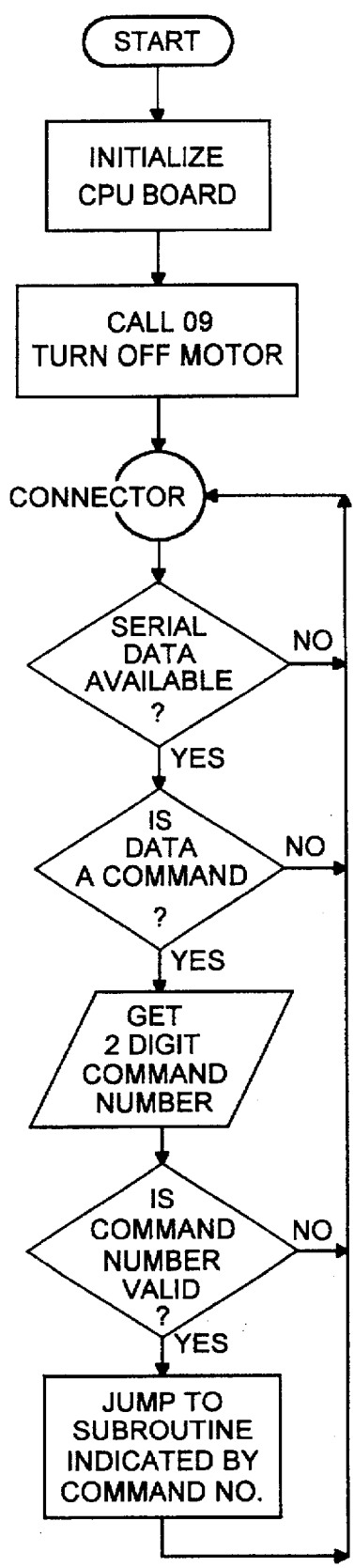
FIG. 4 is a flow diagram of a main routine for a central processing unit used in the lane monitor.
Figure 5:
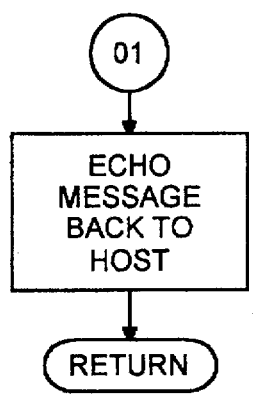
FIG. 5 is a flow diagram of one subroutine for the central processing unit.

An exemplary embodiment of a lane monitor made according to the invention is illustrated in block form in FIG. 1. The same includes a power supply 30 controlled by a power switch unit 32 which may additionally include a fuse and a lamp that is illuminated when the power is turned on. Power is provided to a variety of components in a conventional fashion.

Amongst other things, the lane monitor includes a central processing unit 34, an erasable, programmable read only memory (eprom) 36, a random access memory (ram) 38 and an analog to digital converter 40. An internal clock 42 is also included.

An input to the analog to digital converter 40 is received from a signal conditioner 44 which in turn receives analog signals from a sensor 46 which typically is in the form of a photosensitive device such as a light sensitive diode. The sensor is disposed on one side of a path of tape travel 48 to be described in greater detail hereinafter. On the opposite side, an ultraviolet light source 50 is located and an optical system 52 is associated therewith. The ultraviolet light source 50 may be of the fluorescent type and includes a conventional starting ballast 54 which may be operated by a start switch 56 which is additionally provided with a lamp to illustrate when the ultraviolet light source 50 is operating.

The system also includes a stepper motor 58 of conventional construction that is located adjacent the tape path 48. A roller assembly 60 is disposed adjacent the tape path 48 and is operated by the stepper motor 58. As a consequence, a sample tape disposed in the tape path may be driven through the tape path past the sensor 46 and the light source 50 by being drawn by the roller assembly 60.

A stepper motor driver 62 is operated by the central processing unit 34.

In a preferred embodiment of the invention, the CPU 34 is connected to a conventional RS-232 driver 64 which in turn is connected to a RS-232 serial port 66. The latter provides a means for receiving exteriorally generated commands as well as for outputting data.

In one embodiment of the invention, a conventional personal computer 70 having a display device 72 such as a monitor and/or a printer, may be connected to the port 66 for purposes to be seen. However, the computer 70 could be readily replaced with another CPU if desired.

Turning now to FIGS. 2 and 3, the tape path defining means 48 will be described in greater detail. The same includes an elongated bottom plate 80, and an elongated top plate 82. A pair of spacer plates 84 are disposed between the plates 80 and 82 in spaced relation to each other and thereby define a tunnel-like path for a transparent sample strip or tape. As can be ascertained from the previously identified U.S. Pat. No. 4,487,788, the sample tape will be a double layer made up of two pieces of tape with their adhesive side in contact with one another. One of the tapes will have been applied to the lane to pick-up dressing where the tape was applied to the lane as a result of the dressing adhering to the tape and the second tape is then applied to the first to encapsulate the dressing sample for analysis.

In addition, as mentioned previously, the manner of obtaining the sample assures that part of the tape will have a dressing free leader followed by an opaque section which in turn is followed by the actual sample containing part of the tape.

The leader end of the tape sample is introduced into the aforementioned tunnel at the end 88 thereof.

At the opposite end, the roller assembly 60, is provided. The roller assembly 60 includes a drive roller 92 and an idler roller 94 which are journaled for rotation about horizontal axes adjacent the end 96 of the tunnel opposite the end 88. As seen in FIG. 2, the stepper motor 58 has an output shaft 100 coupled to the drive roller 92.

Intermediate the ends 88 and 96 of the tunnel, the plates 80 and 82 are apertured. Abutting the plate 82 is an ultraviolet transmitting, visible light absorbing filter 102. Just above the filter 102 is an ultraviolet light generating tube 104 which together with a reflector 106 acts as the ultra violet light source 50 (FIG. 1).

Below the lower plate 80 is a diode and filter assembly 46 which includes a photo diode 108 disposed below a final filter 110.

Both the filter 102 and the filter 110 are commercially available. The former has a high transmittance in the wave length range from 300 to 400 nanometers, peaking at 360 nanometers. The latter is a glass-plastic laminated filter available from Schott Glass Technologies, Inc. of Duryea, Penn. The same possesses a long pass character with a very steep curve and very low inherent fluorescence and thus is ideally suitable as a fluorescence barrier filter. The filter identified as KV-418 by the manufacturer is preferred. The photo diode may be a VTS-73 photo diode.

In one embodiment of the invention, the personal computer 70 acts as a host to provide overall control of system operation. That is to say, the personal computer 70 provides exteriorally generated commands to the central processing unit 34, which in turn controls the apparatus in manner to be described.

Generally speaking, an operational sequence, including control functions performed by the personal computer 70 is as follows:

1. User turns on power to Lane Monitor through power switch 32.
2. User turns on U.V. bulb via momentary switch 56.
3. U.V. switch 56 lights to indicate that U.V. bulb is on inside the unit.
4. User connects Lane Monitor to computer via RS 232 serial port 66.
5. User readies the computer/program by loading the control program in the PC 70 and running it.
6. Computer 70 checks if serial port 66 is connected to Lane Monitor and gives error message if it does not receive expected return echo.
7. Computer senses if U.V. light 50 is on and prompts user if light has not been switched on.
8. Control program indicates that the lane monitor is warming up and gives an estimate of warmup time required.
9. Menu allows use to enter lane statistics, load previous lane data for viewing, analyzation, or printing.
10. After the control program has determined that the Lane Monitor is sufficiently warmed up (30–45 minutes), it will prompt user that the lane monitor is ready to calibrate and add "Calibrate" to the menu.
11. When the user selects "Calibrate" from the menus:
    A. Control program prompts user to insert calibration strip into tape path 48.
    B. Control program prompts user to enter value of calibration strip.
    C. Control program reads the calibration strip.
    D. Control program prompts user to remove the calibration strip and press "Enter".
    E. Control program reads zero value.
    F. If last three calibration settings were close, set linearity based on one calibration strip. This calibration setting is saved. Prompt user that basic calibration is complete and unit is ready to read a tape.
    G. If last three calibration setting were not close or if user selects "Long Calibration", repeat above steps A–E for two additional calibration strips.
    H. If linearity of three calibration strips is acceptable, save calibration setting, and prompt user that long calibration is complete and unit is ready to read a tape.
    I. If linearity of three calibration strips is not acceptable, prompt user that one of the calibration strips must be too old. Suggest trying a new set and repeat long calibration or continue with warning message on all data that readings were made with calibration out of range.
12. When the user selects "Read Tape" from the menu:
    A. Control program prompts user to insert front of tape into tape path 48 and hit the "enter" key.
    B. The tape motor starts and positions the tape by sensing the edge of the lane edge marker and backing up 1". (If the reader does not sense the lane edge marker in the first 8 inches, prompt the user to check if correct end of tape was inserted into the tape slot and add lane edge marker if necessary.)
    C. The Lane Monitor reads the header on the tape and adjusts for the U.V. for the tape with no oil. Then the tape drive advances the tape sample ahead approximately 2 inches so the sensor is just beyond the lane edge marker in the sample containing portion of the tape sample.
    D. The unit takes 3 or 4 readings per board and averages them. The average value for each board is sent to the computer.
    E. After the last board is read, the full lane width will be displayed in a two dimensional graph on the monitor 72 with digital values for each board listed in a column to the side of the graph.
13. When the user selects "Enter Lane Statistics" from the menu:
    A. Control program prompts the user to enter the lane number, distance from the foul line, date and time tape was recorded, establishment name, person who recorded lane reading, number of lines bowled since lane was last conditioned and other comments.
14. When the user selects "Print" from the menu:
    A. The control program executes the equivalent of the "Print Screen" command.
15. When the user selects "File Save" from the menu:
    A. The control program first checks that the lane number, distance from the foul line and date were entered in the lane statistics and prompts the user to enter any missing information. If more than one lane width of information is displayed on the monitor, the control program will prompt the user that only the 'base' file will be saved.
    B. The control program then suggests a standard file name and allows the user to change the name before saving the file.
16. When the user selects the "File Open" from the menu:
    A. The control program first prompts the user to save the current file before opening a new file.
    B. The control program first gives the options of erasing the currently displayed information or comparing the new file to the current one.
    C. If the "erase" option was selected, the control program loads the new file and displays it in the same way as if it were being read from an actual tape.
    D. If the "compare" option was selected, the control program loads the new file and displays it on top of the existing monitor display. Only three files (lane width graphs) can be displayed at one time. The graphs will be plotted with different style lines so they can be distinguished on a monochrome monitor or printed on a single color printer. Only the "base" file digital values for each board will be listed in the column to the side of the graph.

The central processing unit 34 performs various functions in response to a series of commands and which are subroutines as depicted in FIGS. 5–15, inclusive. The commands may be verbally described as follows:

>01 Echo back>01 followed by "PC Lane monitor vet X.XX"
>02 Clear Reading(s) area from RAM
>03 Advance the motor 1 step
>04 Advance the motor to get approximately ¼" tape travel
>05 Advance the motor to get approximately 1" tape travel
>06 Reverse the motor 1 step
>07 Reverse the motor to get approximately ¼" tape travel
>08 Reverse the motor get approximately 1" tape travel
>09 Turn off motor current
>10 Take a reading and store in next RAM location
>11 Take a reading and send to computer 70 in 4 hex digits
>12 Take a reading and send to computer 70 in 4 Decimal digits
>13 Send all accumulated readings from RAM to computer 70 as HEX
>14 Send all accumulated readings from RAM to computer 70 as Decimal
>15 Read a tape, readings every approximate ¼" store data in RAM
>16 Read a tape, readings every approximate 1" store data in RAM
>17 Read a tape, readings every approximate ¼" send data to computer 70 in HEX
>18 Read a tape, readings every approximate 1" send data to computer 70 in HEX
>19 Read a tape, readings every approximate ¼" send data to computer 70 in Decimal
>20 Read a tape, readings every approximate 1" send data to computer 70 in Decimal
>21 Place Marker in RAM that all following readings are from a new tape Turning now to FIG. 4, the main routine performed by the CPU 34 will be described. A start signal is received from the personal computer 70 and the CPU board is initialized. Following that, subroutine 9 (FIG. 9) is run to turn off the stepper motor 58. Stepper motors may draw current even when not running and to minimize the heat generated in the chassis in which the various components may be housed, it is desirable that the stepper motor 58 be turned off whenever possible. The next step is to determine whether data is available at the serial port 66. If so, the next question is whether the data represents a command, i.e., one of the numerical commands from 1–21 calling for the performance of a specific subroutine.

If so, the command number is obtained. A check is then made to determine whether the command number is valid. If so, the program jumps to the particular subroutine indicated by the command number.

If, at any time, any one of the questions was answered in the negative, the program loops back to the point where the presence of serial data is checked. Similarly, once any given subroutine is finished, the program loops back to that same point.

Subroutine 1 (FIG. 5) is simply a matter of sending the message back to the personal computer 70. In this way, the program of the personal computer 70 performs function 6, that is, a check whether the connections have been made and provides an error indication if that is not true.

Figure 6:
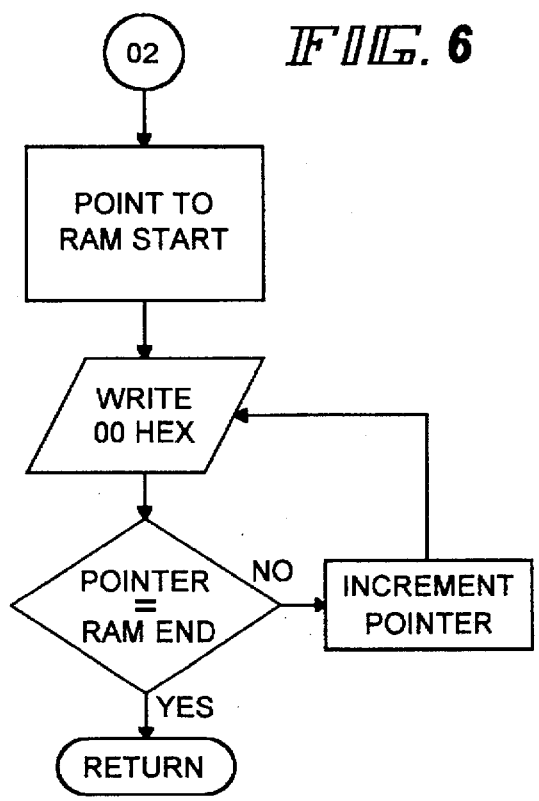
FIG. 6 is a flow diagram of another subroutine.

Subroutine 2 is shown in FIG. 6 is performed when one is desiring to clear information contained in the RAM 38.

Subroutines 3 and 6 are substantially identical save for the fact that subroutine 3 causes the stepper to advance one step (approximately 0.01 inches) and subroutine 6 causes the stepper motor to reverse one step. The basic subroutine common to both is illustrated in FIG. 7. The CPU 34 obtains the motor phase number and then increments the motor phase number by 1. It then outputs the phase code to the motor which advances one step. The new phase number is stored and then the subroutine switches to subroutine 9 to turn off the motor, before returning to the main loop.

Subroutines 4, 5, 7 and 8 differ from one another only in whether the motor is advancing or reversed and only in whether the motor is stepped sufficiently to obtain approximately ¼" of tape travel or approximately 1" tape travel (actually ¹⁷⁄₆₄ inch and ¹⁷⁄₁₆ inch, respectively). It is thus much like the subroutine shown in FIG. 7 except that it has a further inquiry as to whether the required number of steps have been performed along with an appropriate loop to assure that that has occurred.

Subroutine 9 is shown in FIG. 9 and merely amounts to the CPU 34 issuing a signal to the stepper motor driver to turn off the motor and then returning to the main loop.

Subroutine 10 is shown in FIG. 10 and is utilized to obtain a sample. Initially, the analog to digital converter 40 is directed to start converting the analog signal being received continuously on its input to a digital signal. When the conversion is accomplished, the resulting data is stored in the RAM 38 at the location pointed to by the RAM pointer. A return loop is included in the subroutine in the event the conversion from analog to digital has not been fully accomplished when the inquiry is made.

Subroutines 11 and 12 (FIGS. 11 and 12, respectively) are essentially identical in that they both involve taking a reading and outputting the same to the personal computer 70. The difference is that subroutine 11 sends the data to the personal computer 70 in four hexadecimal digits whereas subroutine 12 sends the same information in four decimal digits. The purpose of sending the information in either of two identical ways is simply to allow flexibility in the programming of the personal computer 72 and any appurtenances thereto. In normal operation, only one of the subroutines 11 or 12 will be used and not the other.

Figure 13:
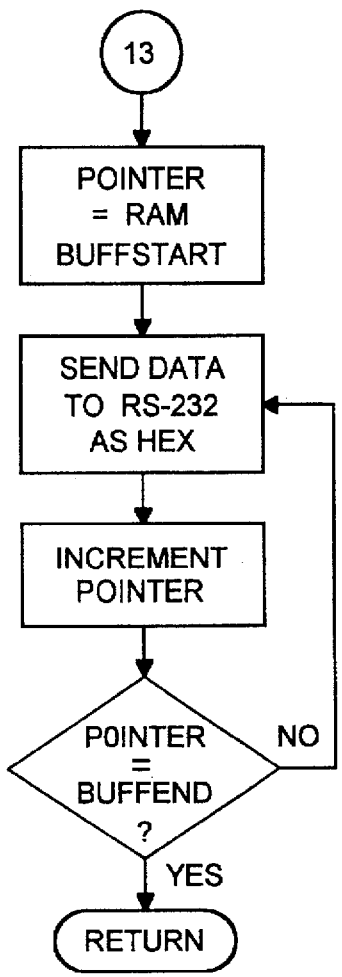
FIG. 13 is a flow diagram for two subroutines.

FIG. 13 illustrates subroutines 13 and 14. The two subroutines are substantially identical except that in one case, subroutine 13, signals are transmitted in hexadecimal form while subroutine 14 transmits them in decimal form. In both cases, the subroutine empties the RAM 38 and transmits its contents to the personal computer 72.

Figure 14:
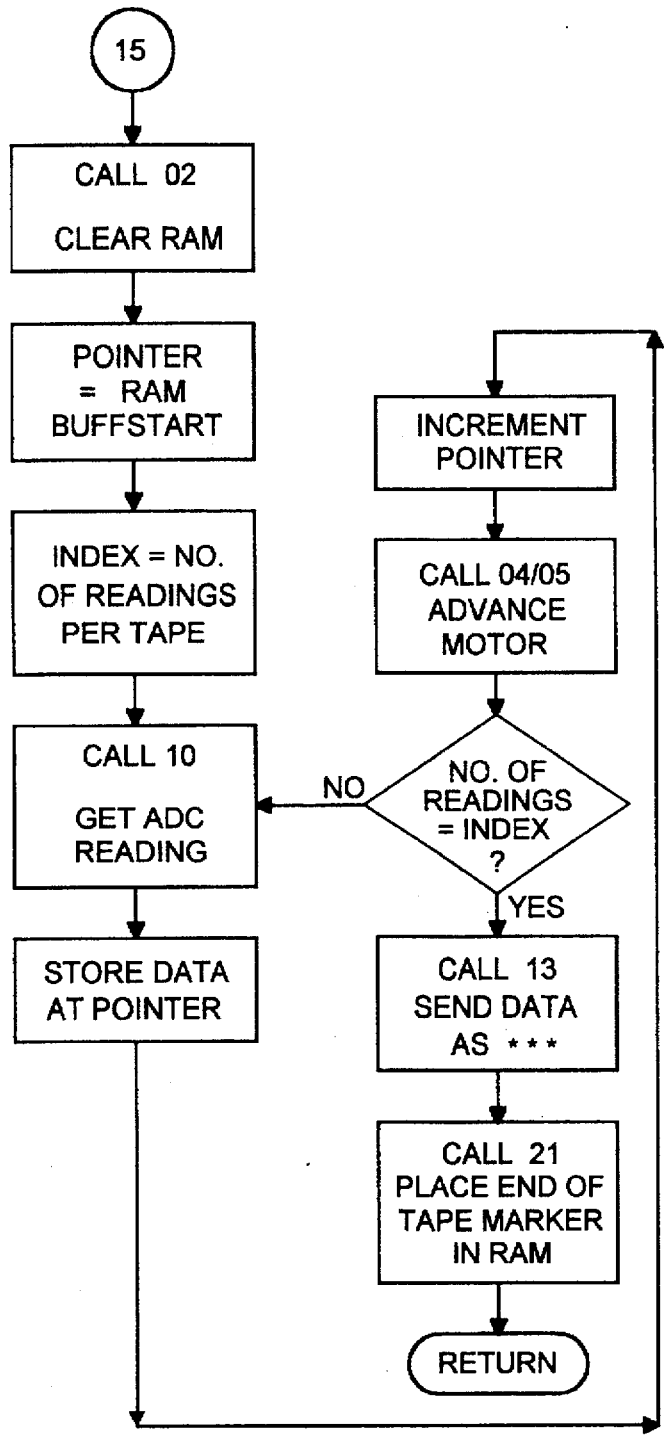
FIG. 14 is a flow diagram for six subroutines.
Figure 15:
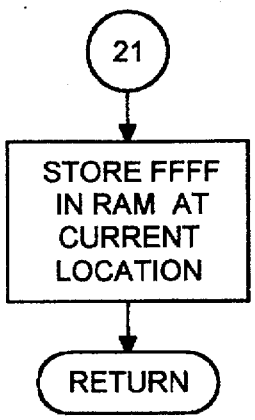
FIG. 15 is a flow diagram for still another subroutine.

FIG. 14 illustrates subroutines 15, 16, 17, 18, 19 and 20. All involve reading a sample tape and either sending or storing sample data. Subroutines 15, 17, and 19 take readings of the tape at every approximate ¼" of tape travel, whereas subroutines 16, 18 and 20 take readings every approximate 1" of tape travel.

Subroutines 15 and 16 cause the data to be stored in the RAM 38 while subroutines 17–20 result in the data being sent to the personal computer 70 in either hexadecimal or decimal form.

The last subroutine, subroutine 21, is illustrated in FIG. 1 and simply amounts to placing a flag in RAM 38 that serves as an indication that all following readings are from a new sample tape.

The main loop and subroutines illustrated in flow chart form in FIGS. 4–15, inclusive are stored in a conventional fashion in the EPROM 36. Returning to FIG. 14, it will be appreciated that the subroutines (subroutines 15–20, inclusive) represented by this figure are of substantial significance in lane analysis. Initially, the subroutine calls for the performance of subroutine 2 (FIG. 6) to clear the RAM 38.

Next, the RAM pointer is set to the start position.

The next step, the number of readings per tape is indicated. This tells whether the reading should be made at ¼" intervals or at 1" intervals.

The subroutine then goes to subroutine 10 to obtain a digital reading from the analog to digital converter corresponding to the analog signal being provided by the photo diode.

Once the reading is obtained, the data is then stored in the RAM 38 at designated locations.

Following that, the pointer of the RAM is indexed or incremented one step in readiness to receive the next reading.

At this point in time, subroutine 4 or 5 is performed to appropriately increment the stepper motor 58.

Following that, a comparison is made of the number of readings taken versus the number of readings to be taken as previously set in the program. If the two are not equal, there is a return subroutine 10 to get another reading from the analog to digital converter. This loop will repeat until such time as the number of readings taken equal the commanded number of readings.

When those two are equal, subroutine 13 is then performed if the information is to be sent in hexadecimal form. Alternatively, subroutine 14 is performed if the information is to be sent in decimal form.

Upon that being completed, subroutine 21 is performed to place a flag indicating that any following data is from a new tape. There follows a return to the main loop.

Flow diagrams for control of the personal computer 70 (or other CPU) to cause the same to execute those commands necessary to perform those functions listed as systems functions 1–17 inclusive, are illustrated in FIGS. 16–22. FIG. 16 illustrates the main loop program for the personal computer 70 and with reference to FIG. 16a, it will be seen that upon start up, it commands the CPU 34 to perform its subroutine 1. This accomplishes system function 6 in that if the echo back is not received, then the personal computer 70 recognizes that it is not properly connected to the serial port 66.

Assuming that the proper connection is established, the personal computer 70 then commands the CPU 34 to perform its subroutine 12. The photo diode 108 is read and if its decimal value is less than a predetermined threshold value, a prompt is given to the user, directing the user to turn on the ultraviolet light 104. This performs function 7 within the system.

Once it is established that the ultraviolet light 104 is active, a prompt is given to the user to indicate that the light 104 is warming up for stabilization purposes and indicating that a limited number of the functions of which it is capable may be performed. Specifically, at this point, the user has the opportunity to select subroutines for the personal computer 70 that (1) enter lane statistics, (2) open an existing lane file, (3) print, or (4) view.

Figure 16A:
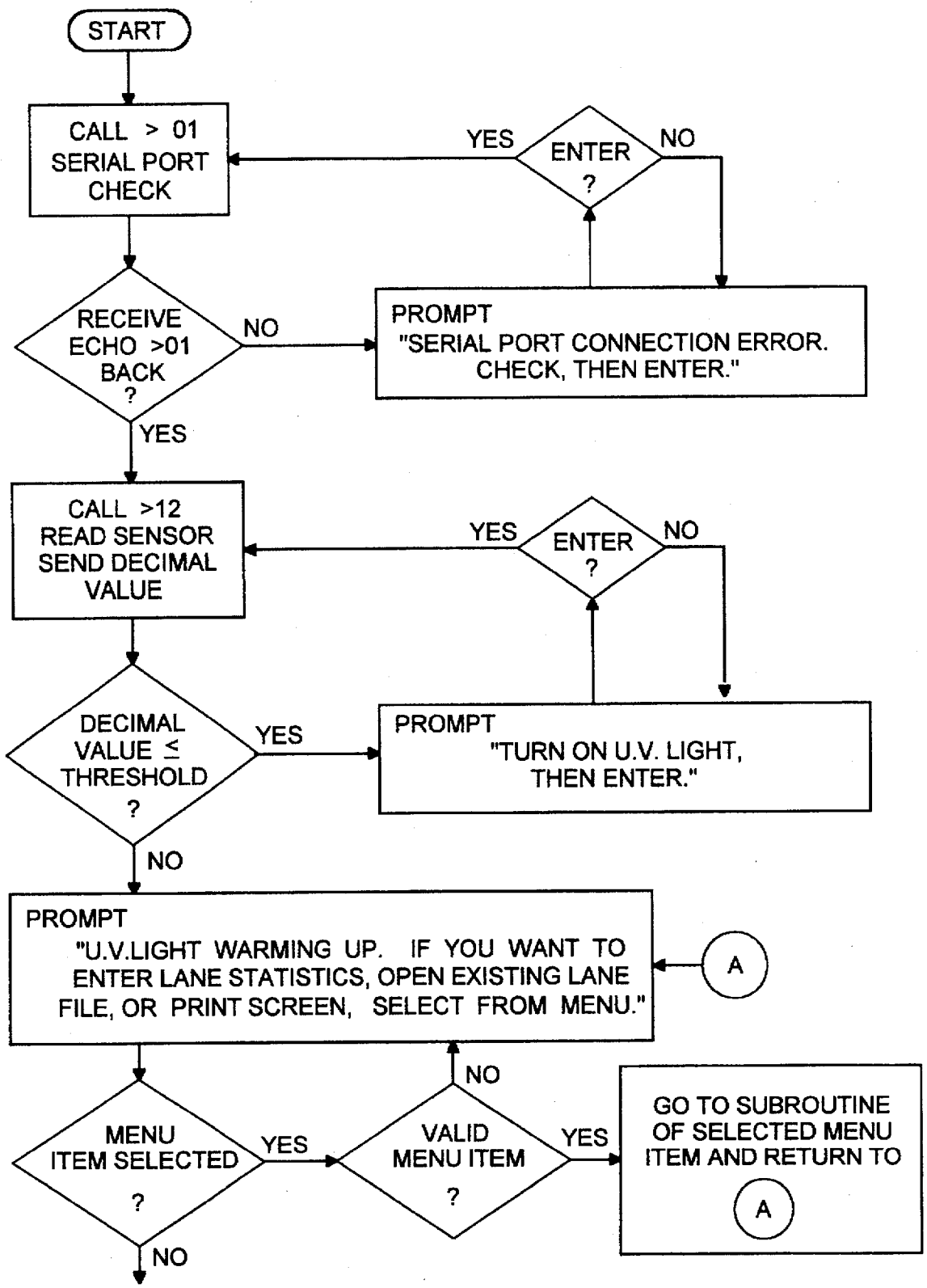
FIG. 16 is a flow chart of the main program loop for a personal computer or other central processing unit and is made up of FIGS. 16a, 16b, 16c, 16d and 16e.

If a subroutine is selected, the personal computer 70 jumps to that selected subroutine, performs it and then returns to the prompting point as indicated in FIG. 16a. This performs system function 9.

Figure 16B:
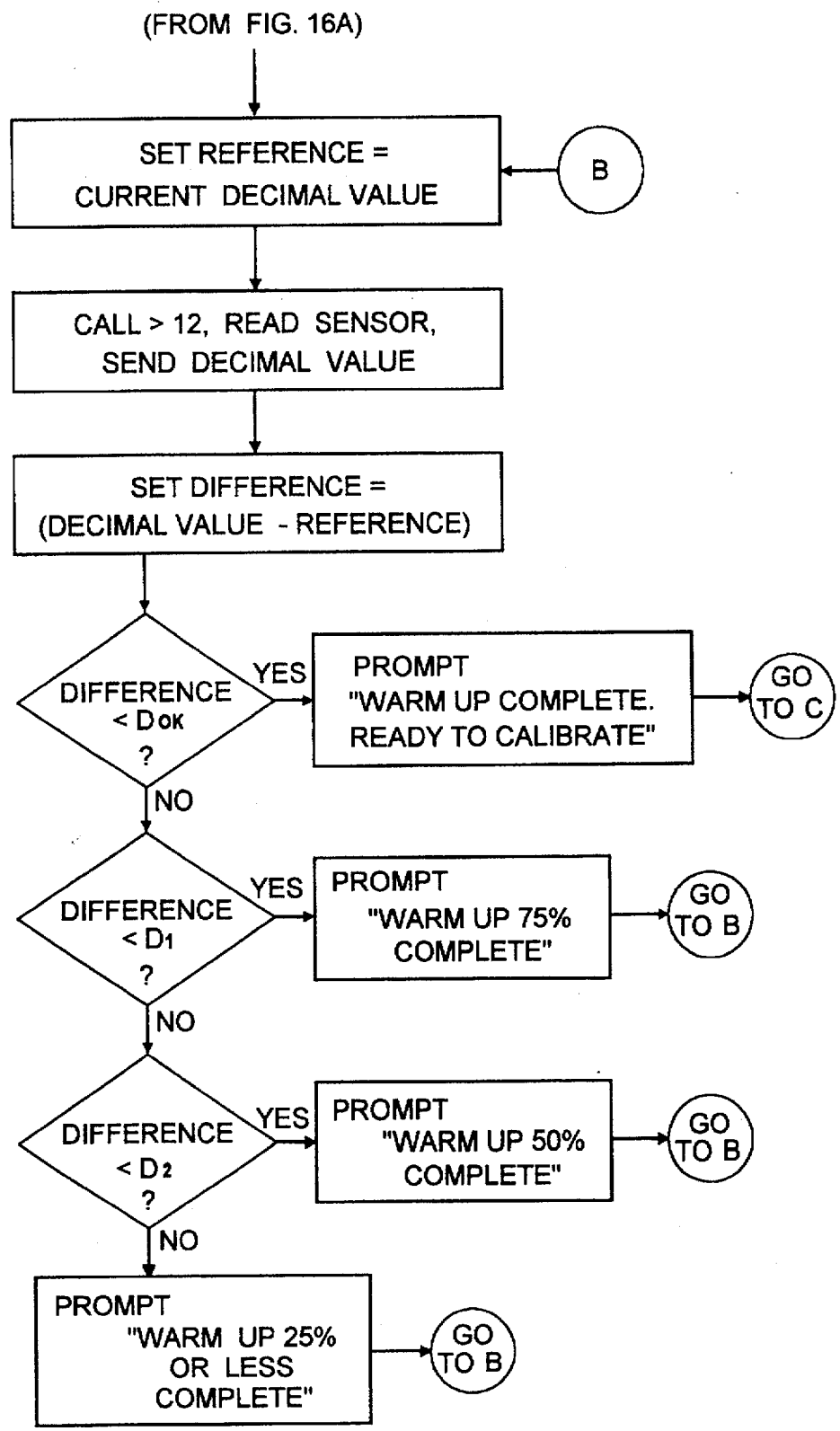

Viewing FIG. 16b, a reference value is set and is the reference value against which the signal from the photo diode 108 will be judged. The personal computer then calls for the CPU 34 to perform its subroutine 12 which results in a reading of the photo diode 108 and the sending of a decimal value corresponding to that reading to the personal computer 70. The reference value is then subtracted from the decimal value and a difference inspected. If the difference is less than some predetermined difference which is sufficiently small for the system to operate, a prompt will issue advising the user that the warm up is complete and that the apparatus is ready to be run through the calibration procedure. If the difference is less than some predetermined magnitude, somewhat greater than the first reference difference, a prompt will be generated indicating that the warm up is approximately 75% complete. Similarly, if the difference is even greater, a prompt will be issued to indicate that the warm up is only 50% complete and if the difference is even greater than that, a prompt is issued to indicate that the warm up is no more than 25% complete.

Figure 16C:
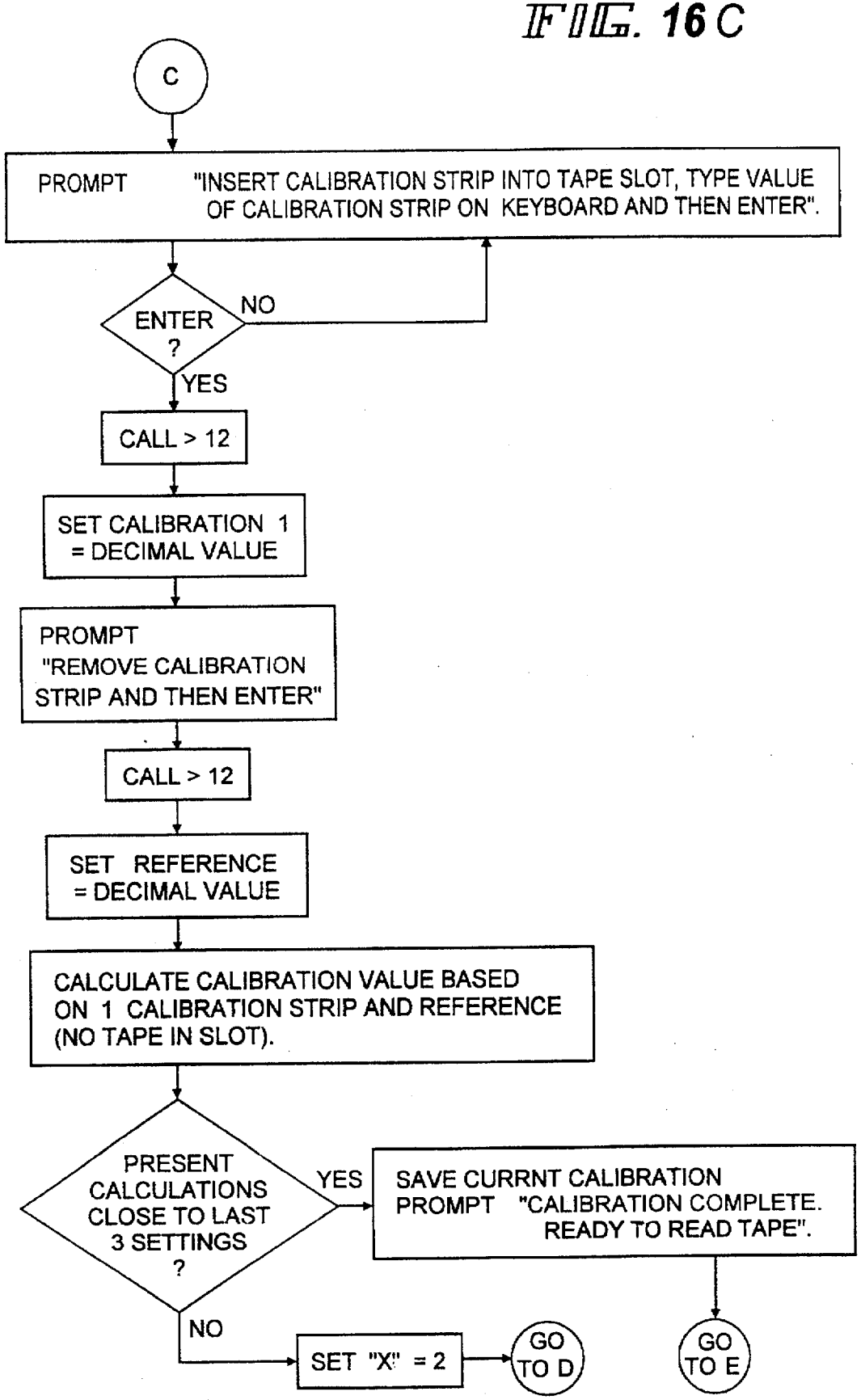

In the case where the warm up is not complete, on each occasion there is a return to the point where the reference decimal value is set. On the other hand, where warm up is complete, the system proceeds to issue a prompt respecting performance of the calibration system as illustrated in FIG. 16c.

As is known in prior art devices, calibration sample strips are provide that are to generate known values when subjected to the system. Calibration strips have their value indicated thereon. Thus, the prompt illustrated in FIG. 16c requests the user to place the calibration strip into the tape path 48 and enter the value thereof on the keyboard for the personal computer 70.

Once properly entered, the CPU 34 is directed to undergo its subroutine 12 so that the calibration strip will be read and the sensed value sent back to the personal computer 70. This calibration is then set to equal the decimal value received.

The user is then prompted to remove the calibration strip and subroutine 12 is again run by the CPU 34 to set a reference value with no tape in the slot.

The machine then calculates the calibration value based on the one calibration strip and on the reference value. If that calibration is close to the calibrations obtained the last three times the apparatus was calibrated, the current calibration is saved for future use and the user is advised that the calibration is complete.

Figure 16D:
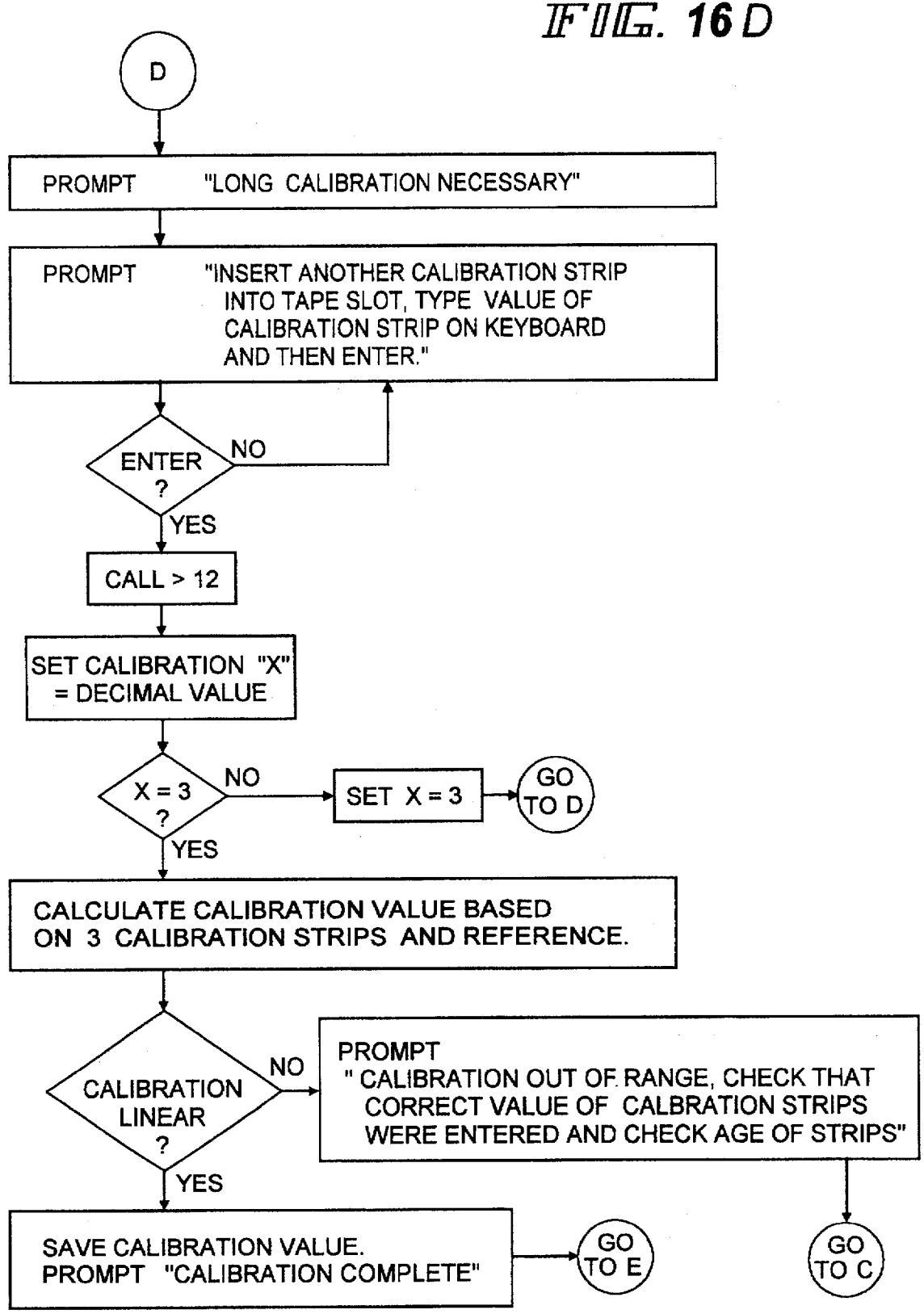

On the other hand, if the present calibration is not close to the last three settings, the procedure continues to that shown in FIG. 16d which is a "long calibration" procedure. As can be readily ascertained from the flow diagram in FIG. 16b, three different calibration strips are used and the final calibration is then based on the values obtained with those three calibration strips and the reference value with no tape in the slot.

Included is a branch that can advise when the calibration is out of the given range. On occasion the age of the calibration is so great that the strips should be changed and fresh ones used. It is also possible that a wrong value was entered. This prompt advises the user to check both possibilities.

Figure 16E:
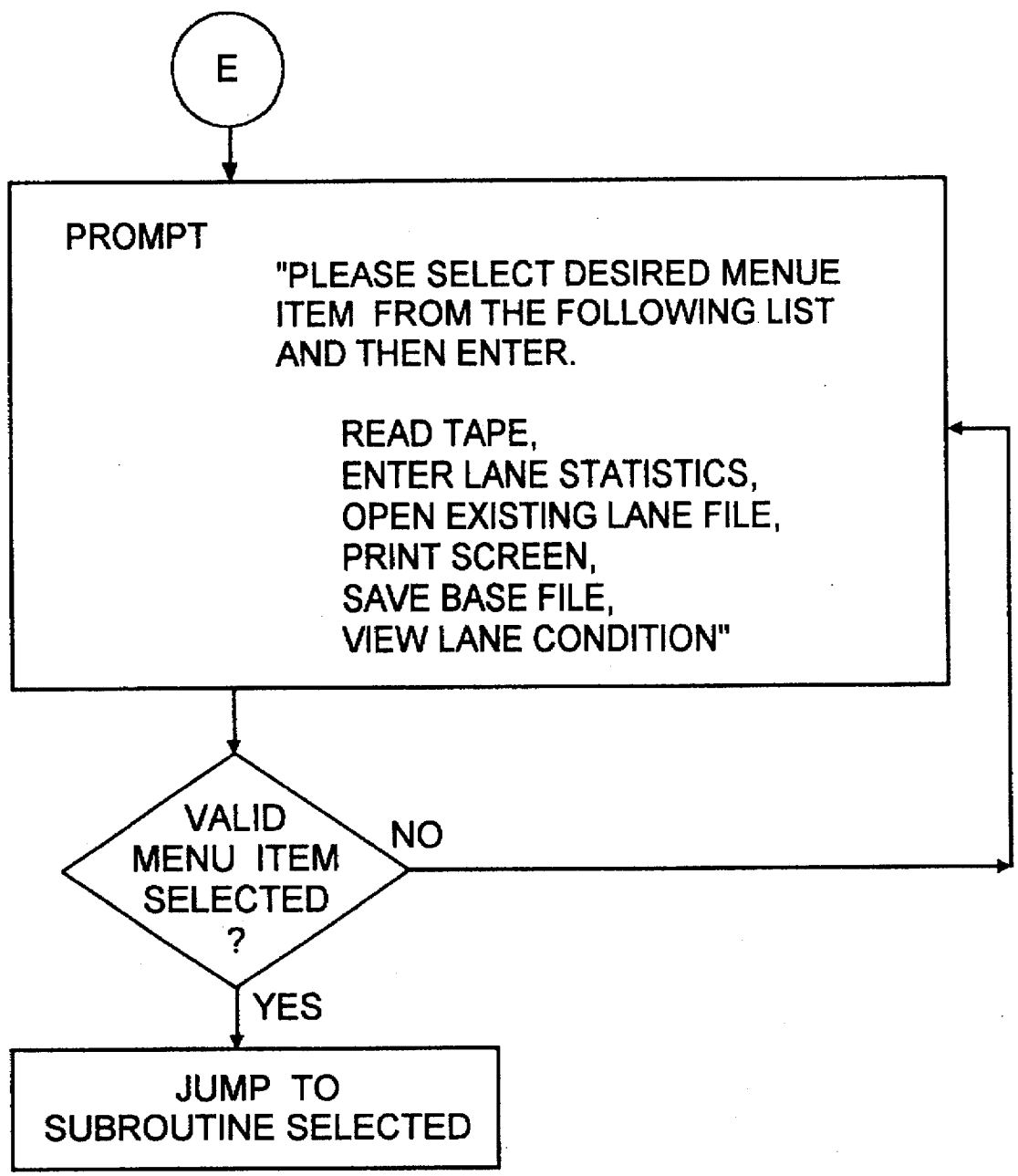

When the calibration complete prompt is given either as a result of performing the functions shown in FIG. 16d or in FIG. 16c, the main loop proceeds to FIG. 16e which asks the user to select a given menu item. Once a valid menu selection has been made, the loop then shifts to the appropriate one of the subroutines for that menu item, which subroutines are depicted in flow chart form in FIGS. 17–22, inclusive.

Figure 17A:
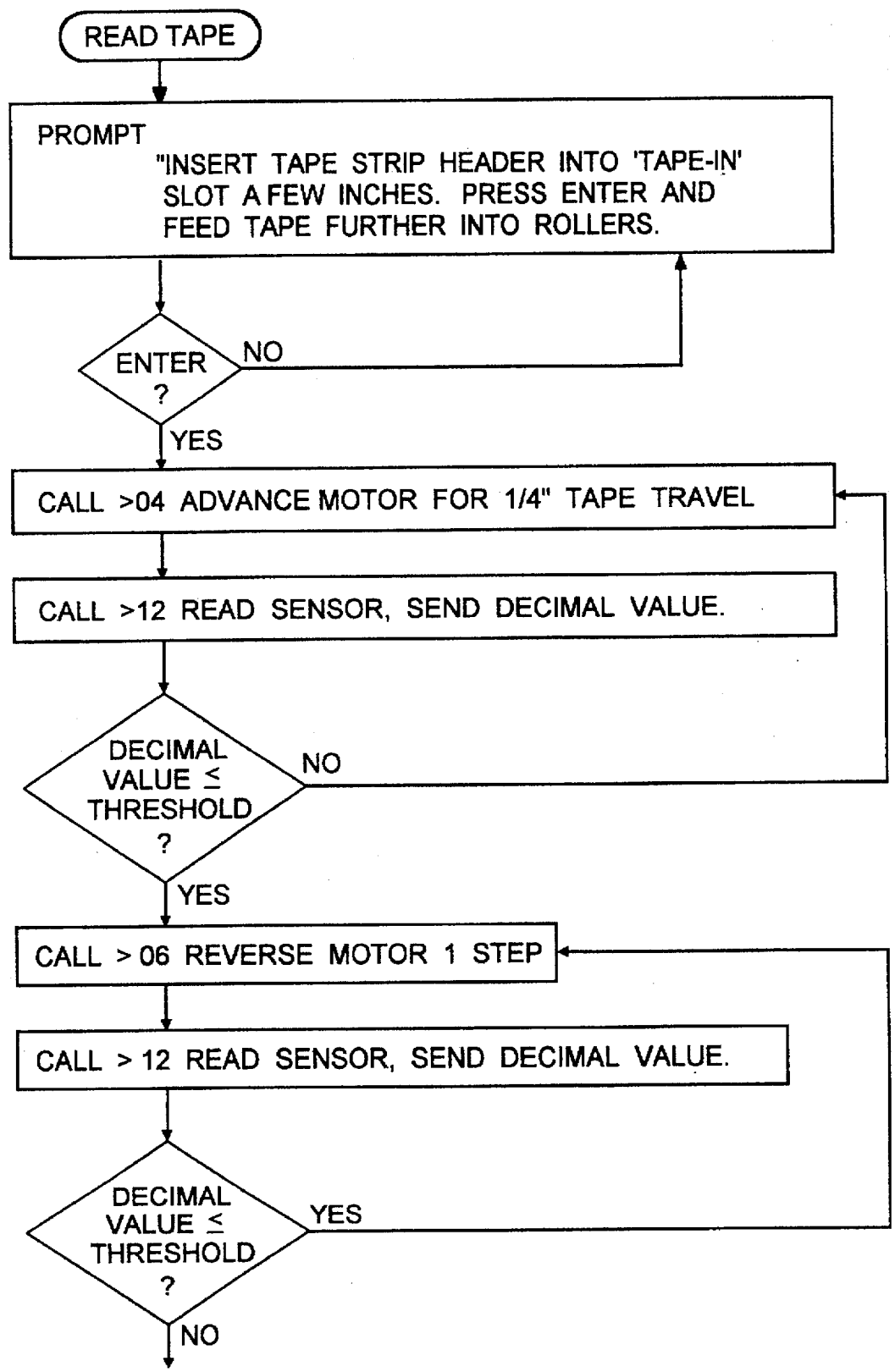
FIG. 17 is a subroutine employed in sampling for operating the personal computer and is made up of FIGS. 17a, 17b and 17c, with FIG. 17a placed above FIG. 17b, which in turn is placed above FIG. 17c.
Figure 17B:
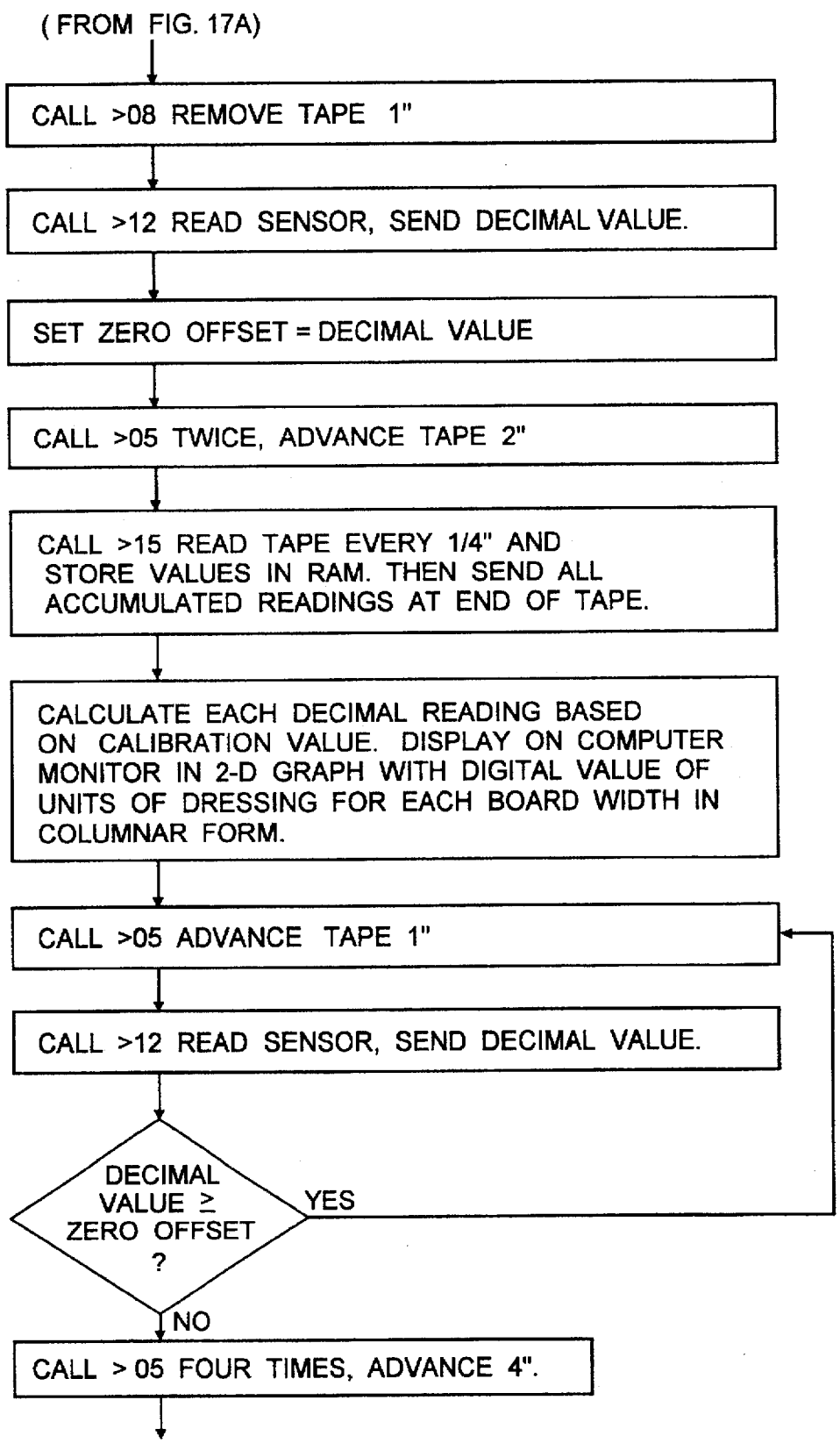
Figure 17C:
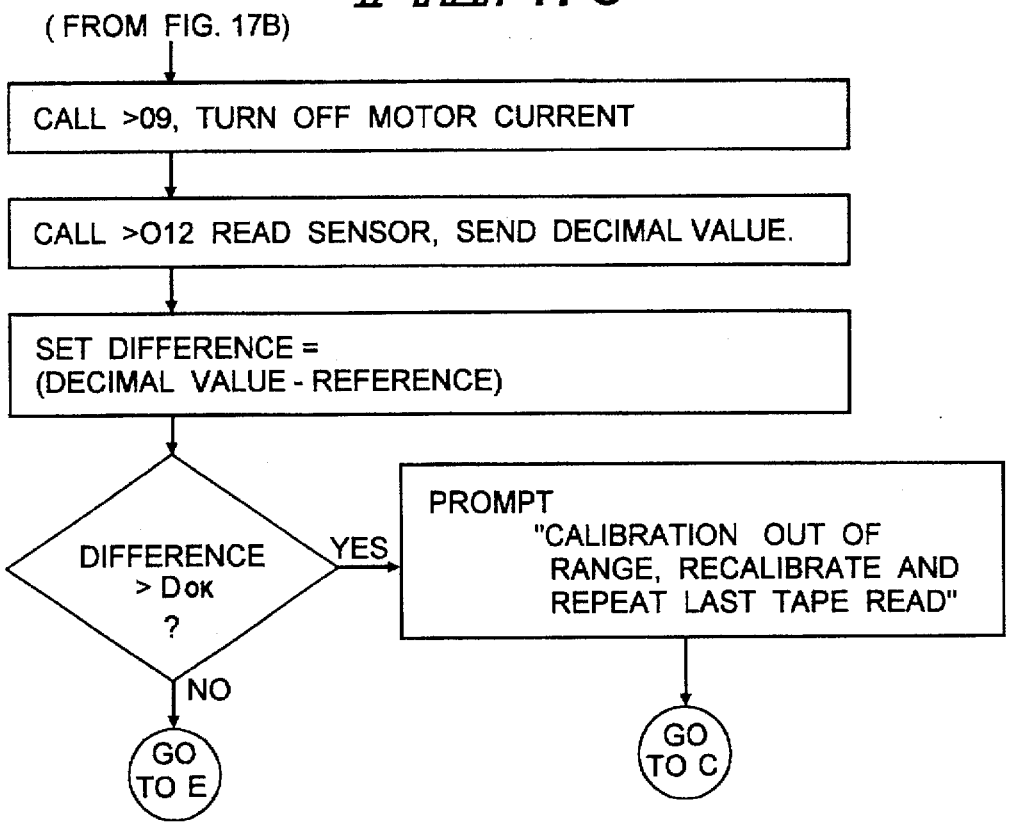

A first of the subroutines is entitled "read tape" and is performed for the purpose of analyzing the sample tape to provide information relative to dressing levels from one edgeboard of the lane to the other. This subroutine is illustrated in FIG. 17 and once started, issues a prompt to the user to insert the tape strip header into the tape path 48. Once the sample tape has been properly entered, the CPU 34 is commanded to perform its subroutine 4 which is to advance the stepper motor for ¼" tape travel. That is followed by subroutine 12 which reads the photo diode 108 and sends the decimal value of the reading back to the personal computer 70.

If the decimal value is not equal to or less than a threshold value, both subroutines are repeated sequentially until such occurs. The point of this process is to locate the lane edge marker placed on the sample strip at the time the sample is taken to enable the sample strip to be properly read from one lane edge to the other.

When the decimal value is less than or equal to the threshold value, subroutine 6 is performed to reverse the stepper motor 58 one step which may correspond, for example, to a distance equal to about 0.01". Subroutine 12 is then performed once again followed by a determination of whether the read decimal value is less than or equal to the threshold value. If the answer is "yes", subroutines 6 and 12 are sequentially repeated, backing the tape in ¹⁄₁₀₀th of an inch increments for each repeat to find the exact location of the edge of the lane marker.

When that is finally accomplished, subroutine 8 is performed which requires the backing out of the tape a full inch. At this point, a part of the tape in the leader that has not been in contact with the lane to pick up dressing is in a position to be read by the sensor. Accordingly, subroutine 12 is performed and the resulting decimal value is sent to the personal computer 72. It in turn sets the "0" offset an amount equal to the decimal value just received.

The purpose of the foregoing sequence is to read the natural fluorescence of the sampling tape and provide an adjustment in future readings to offset the natural fluorescence of the tape.

After that has been accomplished, subroutine 5 is run twice to advance the tape at a total of approximately 2" for the purpose of returning to the edge of the tape whereat the sample portion thereof begins. Thereafter, subroutine 15 is performed, causing the sample tape to be analyzed every approximate ¼" with the resulting readings being stored in the RAM.

That is followed by a calculation of each decimal value based on the calibration value and the reading. The result is displayed on the computer monitor as a two dimensional graph with digital values of the units of dressing according to the ABC definition for each board width. The display is in columnar form, with one column of 39 rows, one for each board in a conventional lane.

Following that, the CPU 34 is directed to perform subroutine 5 followed by subroutine 12 which is for the purpose of advancing the tape until the tape is clear of the apparatus. The exact procedure is listed in FIG. 17b.

Once the tape is clear of the apparatus, subroutine 9 is performed to turn off the stepper motor 58 and that is followed by subroutine 12 to enable a determination of the difference between the resulting decimal value read and the reference value. If the difference is greater than the desired difference, a prompt is issued calling for recalibration and repetition of the last reading procedure. The program then goes to point 'C' in the main routine for the personal computer 70 as shown in FIG. 16c.

If the difference is not greater than the predetermined difference, then the program returns to point 'E' of the main routine as found in FIG. 16e.

Figure 18:
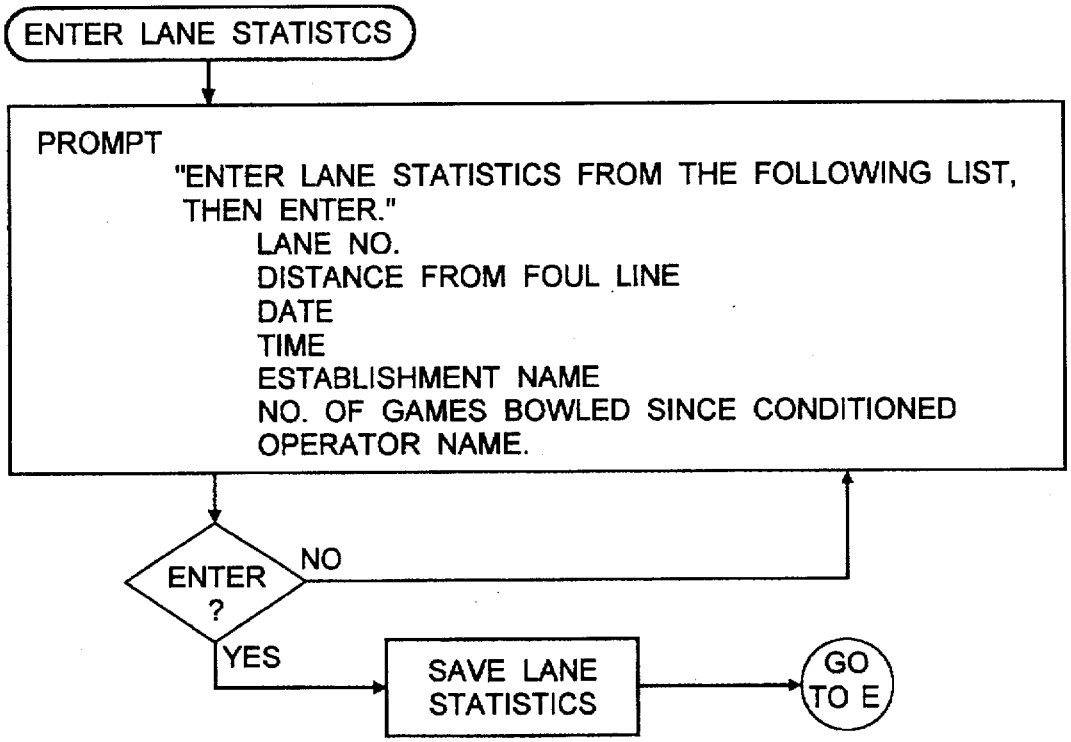
FIG. 18 is a flow diagram of a subroutine for entering lane statistics into the system.

The "enter lane statistics" subroutine is illustrated in FIG. 18 and if selected (FIG. 16e), causes a prompt to be issued such that the user is asked to enter lane statistics from a list of statistics which include the lane number, the distance from the foul line at which the sample was taken, the date and time of the taking of the sample, the name of the bowling establishment, the number of games bowled on the lane since it was last conditioned, and the operator name. If the statistics are not entered, the prompt remains whereas if the statistics are entered, a command is issued to save the lane statistics at the personal computer 70 and then the program returns to point 'E' on the main routine (FIG. 16e).

Figure 19:
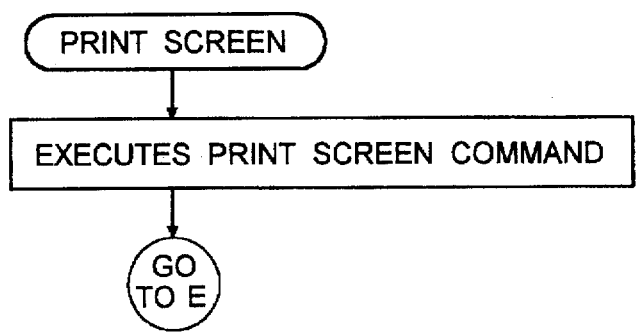
FIG. 19 is a flow chart of a subroutine for printing information.

The "print screen" subroutine is illustrated in FIG. 19 and when selected, merely amounts to the execution of a conventional print screen command at the PC. When completed, the subroutine returns to point 'E' in the main routine.

Figure 20:
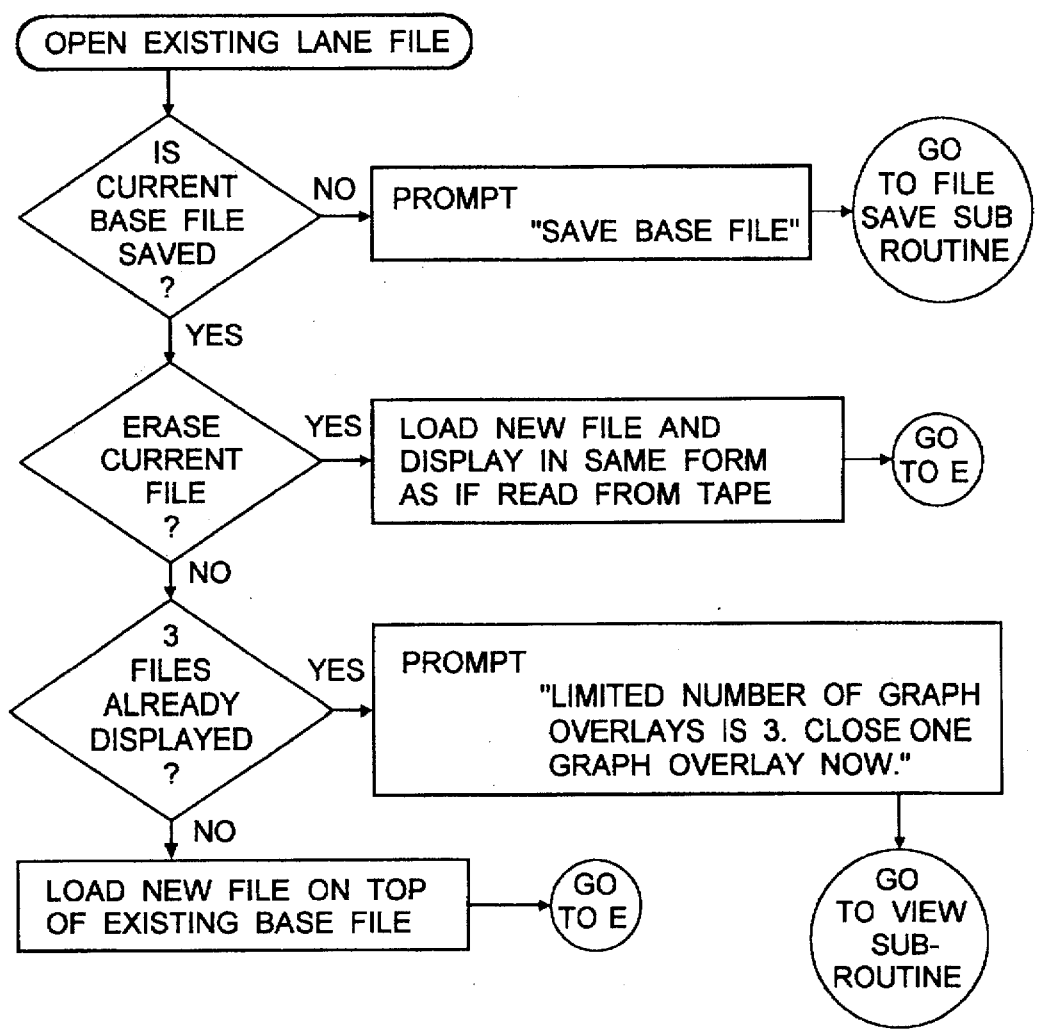
FIG. 20 is a flow diagram of a subroutine relating to opening of a lane file.

The "open existing lane file" subroutine is illustrated in FIG. 20 and when selected immediately determines whether the current base file has been saved. If not, the user is prompted to save the base file and the subroutine proceeds to the "file save" subroutine illustrated in FIG. 21 and to be described hereinafter. Assuming, however, that the current base file has been saved, the user is queried whether the current file is to be erased. If yes, the new file is loaded and displayed and the subroutine returns to point 'E' (FIG. 16e) of the main routine. If no, a determination is made as to whether three files are already displayed. If the answer is yes, a prompt is issued advising the user that only a limited number of graph overlays may be displayed and that one graph overlay must be removed. The subroutine then proceeds to the "view" subroutine shown in FIG. 22 and to be described hereinafter.

On the other hand, if three files are not already displayed, the new file can be loaded on top of the existing base file and the subroutine returns to point 'E' of the main routine.

Figure 21:
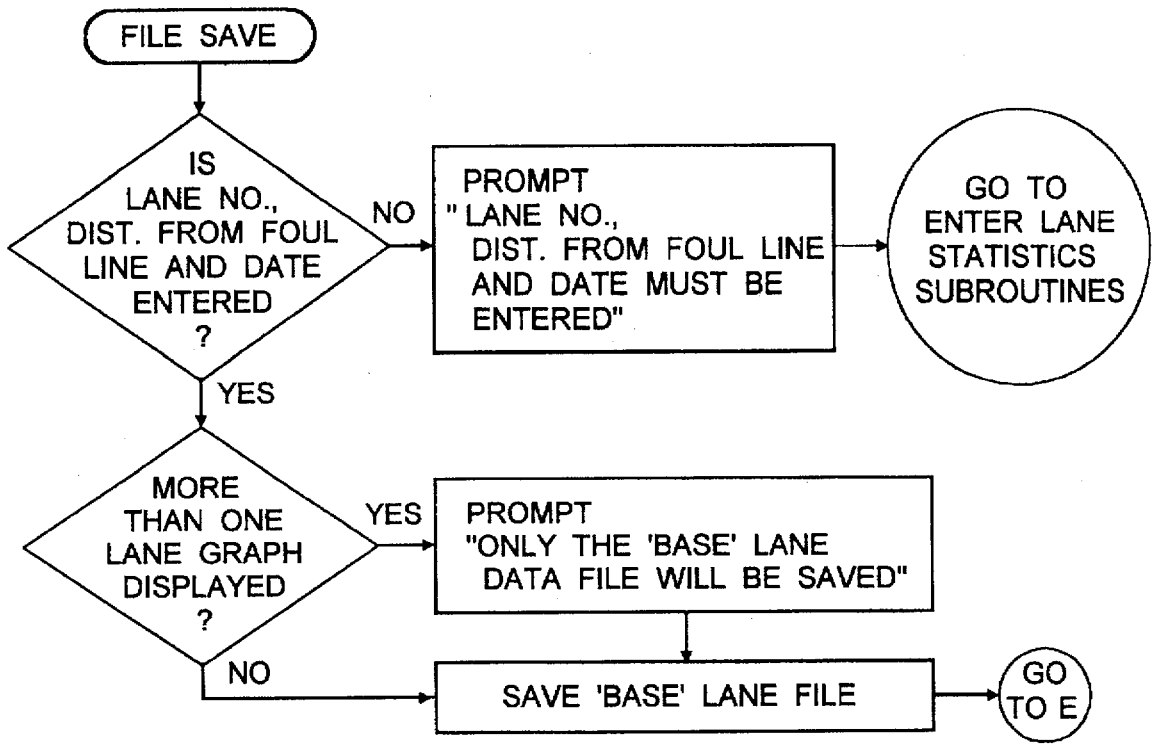
FIG. 21 is a flow diagram of a subroutine employed to save a file.

The "file save" subroutine referred to earlier as illustrated in FIG. 21 and when selected first queries whether the lane number, the distance from the foul line, and the date of sample has been entered. If the answer is no, the user is prompted to that effect and the subroutine branches to the "enter lane statistics" subroutine illustrated in FIG. 18 and described previously.

If the information has been entered, query is then made whether more than one lane graph is displayed. If the answer is yet, the user is issued a prompt to advise him that only the base lane data file will be saved. The program then causes the base lane file to be saved and the subroutine returns to point 'E' (FIG. 16e) of the main routine.

If, on the other hand, only one lane graph is displayed, the routine proceeds to save the base lane file and then returns to point 'E' as before.

Figure 22:
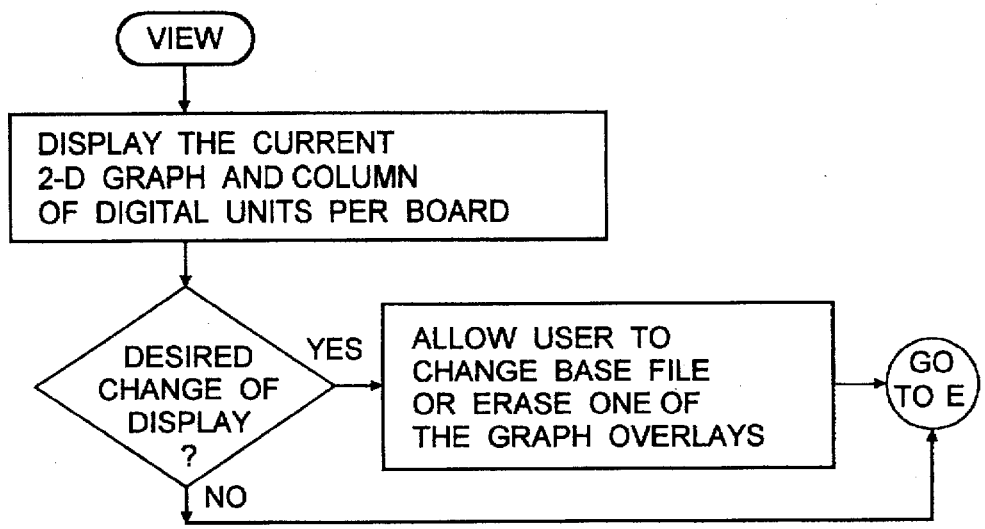
FIG. 22 is a flow diagram employed to cause a display on a computer monitor.

The "View" subroutine is illustrated in FIG. 22 and initially, when selected, causes the display of the current two dimensional graph and the column of digital units. A query is then generated as to whether a change of the display is desired.

If the answer is no, the subroutine returns to point 'E' of the main routine. If the answer is yes, the user is permitted to call up a different base file and/or erase a graph overlay. When that is accomplished, the subroutine returns to point 'E' of the main routine.

From the foregoing, it will be appreciated that a lane monitor made according to the invention possesses substantial advantages over those heretofore known. For one, by sampling as frequently as every ¼" of tape, one can effectively obtain four readings per board across the width of a bowling lane. Consequently, one aberrant reading will not have a material effect on the accuracy of the information obtained because it may be taken into account with several other readings for the same board.

In addition, through the automatic indexing of the sample tape an automatic sampling thereof under the direction of the CPU 34 controlled by the algorithms or subroutines stored in EPROM 36, data may be much more rapidly acquired than with prior art devices, thereby shortening the sampling process substantially. This in turn makes it easier to use the machine. This in turn will likely result in more frequent use of the machine by bowling lane proprietors and that ultimately will assure that lanes that have been certificated by the appropriate governing body will be more likely to be up to standard at any given point in time.

Even more significantly, the ease of use makes it feasible to utilize the monitor daily as a maintenance tool. When so used, a consistent lane condition can be assured. As a consequence, bowlers using the lanes will be more satisfied because of their consistent condition and the consistency factor itself enables the bowlers to obtain higher scores. Consequently, the use of the lane monitor is cost effective in that it results in a greater number of satisfied customers and that in turn results in the generation of additional business.

Furthermore, the ability to connect to a personal computer or the like provides the capability for providing computer generated comparative charts, or even simply charts showing dressing levels from 1" of the lane to the other for each point on the lane whereat samples are taken without painstakingly manually indexing the tape strip, reading an analog driven meter indicating the dressing level, and graphically or otherwise recording the same manually.

Although not specifically described herein, it should be apparent that the invention is not limited to one wherein a fluorescing additive is added to the lane dressing material which is being analyzed. For example, the lane dressing could be formulated utilizing a metal or magnetic additive or an optically sensitive additive other than an ultraviolet light sensitive additive. The additive could then be analyzed using a metallic, polarized or magnetic sensor.

We claim:

1. In an apparatus for monitoring the dressing on the surface of a bowling lane, the combination of:
   a sensor for sensing a characteristic of a dressing sample and providing a signal representative thereof;
   means for effecting relative movement between said sensor and a dressing sample;
   means for operating said sensor and said relative movement effecting means to sense a dressing sample and to issue signals at a predetermining rate per a predetermined increment of relative movement between said dressing sample and said sensor effected by said relative movement effecting means; and
   means for collecting said signals and for storing values representing the same.

2. The apparatus of claim 1 wherein said sensor is a single sensor and said operating means includes means for initially operating said sensor to sense said characteristic in the absence of a dressing sample and undergoing a calibration routine, and thereafter operating said sensor and said relative movement effecting means to sense a dressing sample.

3. The apparatus of claim 1 wherein said relative movement effecting means comprises means for moving a sample containing element past said sensor.

4. The apparatus of claim 3 wherein there is a single sensor and wherein the sample containing element includes a leader section and a sample containing section; and said generating means includes means for a) initially operating said sensor in the absence of a sample containing element and thereafter in the presence of the leader section to sense said characteristics in the absence of (i) both a dressing sample and a sample containing element, and (ii) a sample containing element only for calibration purposes, and b) thereafter operating said sensor and said moving means to sense said characteristic in a dressing sample as said sample containing portion is moved past said sensor by said moving means.

5. The apparatus of claim 1 wherein said sensor is a single sensor and said operating means operates said sensor to a) initially sense said characteristic on a calibration element, b) thereafter sense said characteristic in the absence of a sample collecting element, and c) thereafter sense said characteristic on a sample containing element.

6. The apparatus of claim 5 wherein said sample containing element is a strip having a sample free leader followed by a sample containing section and said sensor first senses said leader for said characteristic and thereafter senses said sample containing section.

7. In an apparatus for monitoring the dressing on the surface of a bowling lane by sensing a light responsive material in the dressing the combination of:
   a source of light having a particular characteristic and of the type requiring warm up to stabilize;
   a sensor for receiving light and providing a signal whose magnitude varies according to the presence or absence of a response by the material in the dressing when exposed to said source;
   a memory for receiving and storing predetermined information relative to a plurality of bowling lanes as a lane files;
   means for selectively displaying information contained in said receiving and storing means;
   means for entering information in said receiving and storing means; and
   operating means for determining if said light source has not warmed up to stabilization and for enabling operation of said displaying means and said entering means.

8. The apparatus of claim 7 wherein said displaying means comprises a monitor.

9. The apparatus of claim 7 wherein said displaying comprises a printer.

10. The apparatus of claim 7 wherein said operating means includes a central processing unit and a programmed personal computer.

11. In an apparatus for monitoring the dressing on the surface of a bowling lane by sensing a light responsive material in the dressing the combination of:
   a source of light having a particular characteristic and of the type requiring warm up to stabilize;
   a sensor for receiving light and providing a signal whose magnitude varies according to the presence or absence of a response by the material in the dressing when exposed to said source;
   means for calibrating said sensor with a short routine and with a long routine and providing a calibration value;
   means for storing said calibration value;
   means for comparing a calibration value with at least one stored calibration value;
   means responsive to said comparing means for directing said long routine when a difference between said calibration value and said at least one calibration value greater than a predetermined difference exists.

12. The apparatus of claim 11 wherein said short routine determines said calibration value on a single measurement and said long routine determines said calibration value on at least three measurements.

* * * * *